(12) United States Patent
Mattila et al.

(10) Patent No.: US 7,491,364 B2
(45) Date of Patent: *Feb. 17, 2009

(54) METHOD AND SYSTEM FOR TRANSPORTING AND STORING MULTIPLE REAGENT PACKS AND REAGENT PACKS USED THEREIN

(75) Inventors: Robert J. Mattila, Jordan, MN (US); Mark J. Kittock, Eden Prairie, MN (US)

(73) Assignee: Beckman Coulter, Inc., Fullerton, CA (US)

( * ) Notice: Subject to any disclaimer, the term of this patent is extended or adjusted under 35 U.S.C. 154(b) by 939 days.

This patent is subject to a terminal disclaimer.

(21) Appl. No.: 10/860,368

(22) Filed: Jun. 2, 2004

(65) Prior Publication Data

US 2004/0219678 A1 Nov. 4, 2004

Related U.S. Application Data

(63) Continuation of application No. 09/594,331, filed on Jun. 15, 2000, now Pat. No. 6,746,648.

(51) Int. Cl.
*G01N 35/00* (2006.01)
(52) U.S. Cl. .............................. 422/65; 422/66; 422/64; 422/100; 422/63; 436/43; 436/47; 436/48; 436/49; 436/54
(58) Field of Classification Search ............. 422/63–66, 422/100; 436/43, 47–49
See application file for complete search history.

(56) References Cited

U.S. PATENT DOCUMENTS

| | | | | |
|---|---|---|---|---|
| 4,812,392 A | * | 3/1989 | Miyake et al. | 435/3 |
| 5,417,922 A | * | 5/1995 | Markin et al. | 422/65 |
| 6,159,425 A | * | 12/2000 | Edwards et al. | 422/63 |
| 6,746,648 B1 | * | 6/2004 | Mattila et al. | 422/65 |

* cited by examiner

*Primary Examiner*—Brian R. Gordon
(74) *Attorney, Agent, or Firm*—Townsend and Townsend and Crew LLP

(57) ABSTRACT

A new method and system for transporting and sorting multiple reagent packs used in conjunction with an immunodiagnostic instrument is provided. The new system includes a multiplicity of reagent packs; a gantry movably mounted on a rack structure for carrying a gripper mechanism, wherein the gripper mechanism has gripping jaws for engagement with the reagent pack; a power assembly for actuating the respective movement of the gantry, the gripper mechanism and the gripping jaws; a storage nest having a multiplicity of compartments, each adapted for storing a one of the respective reagent packs; and a pipetting nest having a multiplicity of compartment, each adapted for retaining a respective one of the reagent packs for simultaneous pipetting. Methods of using the system and a novel reagent pack used in connection with the new system are also provided.

9 Claims, 8 Drawing Sheets

METHOD AND SYSTEM FOR TRANSPORTING AND STORING MULTIPLE REAGENT PACKS AND REAGENT PACKS USED THEREIN

CROSS REFERENCE TO RELATED APPLICATIONS

This patent application is a continuation of the U.S. patent application Ser. No. 09/594,331, filed on Jun. 15, 2000 now U.S. Pat. No. 6,746,648.

BACKGROUND OF THE INVENTION

1. Area of the Art

The present invention relates generally to reagent handling methods and systems used in conjunction with immunodiagnostic instruments, and more specifically to methods and systems for transporting and sorting multiple reagent packs and reagent packs used in conjunction with the systems.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Immunodiagnostic instruments are widely used in clinical chemistry sampling and analyzing applications, and often are involved in the processing of multiple reagent packs for performing various assays. Many times it is required that the system be capable of receiving and storing multiple reagent packs in a refrigerated environment in such a manner that each stored pack can be randomly accessed and brought from storage into a position for pipetting. It is desirable for this to be accomplished in such a manner that requires minimal footwork and a degree of freedom.

The following references are found to be pertinent to the field of the present invention: U.S. Pat. No. 4,483,927, issued to Takekawa on Nov. 20, 1984, disclosed a conventional automatic chemical analyzer. It includes a reagent delivery unit having a plurality of reagent bottles and a syringe type dispenser for delivering given amounts of reagents into a plurality of empty reaction vessels set in a cassette, and a reaction vessel supply unit for holding a plurality of cassettes and for supplying successively the reaction vessels.

U.S. Pat. No. 4,678,752, issued to Thorne et al. on Jul. 7, 1987, disclosed a conventional automatic random access analyzer. It includes an elongate rack having a plurality of slots aligned in substantially parallel arrangement along the longitudinal axis of the rack for removably positioning reagent packages, an introduction station for receiving the plurality of reagent packages, each having a plurality of receptacles, a liquid transfer station for transferring the receptacles, a storage area for storing the plurality of reagent packages, and a shuttle system for transporting individual reagent packages.

U.S. Pat. No. 4,764,342, issued to Kelln et al. on Aug. 16, 1988, disclosed a conventional reagent handling system. It includes a transport mechanism interengageable with a coupling structure for disposing a series of reagent containers for movement past a reagent station.

U.S. Pat. No. 5,314,825, issued to Weyrauch et al. on May 24, 1994, disclosed a chemical analyzer. It includes a turntable rotatably mounted about a vertical axis and having a plurality of equiangularly spaced radial compartments for releasably mounting a plurality of individually disposable cuvettes, and a sample/reagent tray rotatably mounted about an axis parallel to the turntable axis.

U.S. Pat. No. 5,332,549, issued to MacIndoe, Jr. on Jul. 26, 1994, disclosed an assay module transport apparatus for use in an automated analytical instrument. It includes an assay module supply unit for holding magazines with open-faced vessels, each having a layer of material covering its open face, an assay module ejector mechanism having a slider block and a pusher rod mounted on the leading end of the slider block for pushing an assay module from an assay module supply unit onto an assay module receiving platform, an assay module transfer mechanism for transferring the assay module from the assay module receiving platform to a testing system, and a cutter assembly for cutting the layer of material covering the open-faced vessels.

U.S. Pat. No. 5,578,272, issued to Koch et al. on Nov. 26, 1996, disclosed a reagent kit for use in an automatic analytical apparatus. The reagent kit includes a casing which has a bottom, sidewalls, a removable lid, and at least one individually removable reagent container. The lid defines at least one opening which is of sufficient dimension for circulating air through the interior of the casing and around the reagent container.

U.S. Pat. No. 5,609,822, issued to Carey et al. on Mar. 11, 1997, disclosed a reagent handling system and reagent pack for keeping fluids with or without suspensions, mixed or suspended upon rocking. It includes a tray for slidably retaining a plurality of reagent pack slides in a side by side configuration along an axis, and an inclination drive and hinge mechanically connected to the tray for selectably inclining the tray about the axis and the hinge. U.S. Pat. No. 5,705,074, issued to Katzman on May 12, 1998, disclosed a reagent segment for feeding reagent to the multiple capillaries of the automated capillary electrophoresis apparatus. The reagent segment has an elongated body with an elongated and continuous open trough, a drainage zone in a floor of the trough, and a fill section in the trough sufficiently wide to receive a dispenser probe.

U.S. Pat. No. 5,788,928, issued to Carey et al. on Aug. 4, 1998, disclosed a reagent handling system and reagent packs for keeping fluids with or without suspensions, mixed or suspended upon rocking. The reagent pack has mixing baffles operative to cause mixing of fluids within the reagent pack, where the baffles are disposed in proximity and opposing each other so that a throat region having a pair of converging, then diverging, walls is defined between a pair of baffles.

U.S. Pat. No. 5,955,373, issued to Hutchins et al. on Sep. 21, 1999, disclosed an environmentally controlled system for processing chemical products. It includes a plurality of interchangeable units connected in an array arranged to sequentially receive the products. Each unit has a work station covered by a canopy having at least one open end connected with an open end of an adjacent unit. The interconnected units form an enclosed chamber encompassing the work stations and covered by the interconnected canopies.

U.S. Pat. No. 5,985,214, issued to Stylli et al. on Nov. 16, 1999, disclosed an automated and integrated system for rapidly identifying useful chemicals in liquid samples, and, more particularly, for automated screening of chemicals with biological activity in liquid samples. The system includes at least one multi-lane sample transporter for transporting the addressable chemical wells between the storage and the sample distribution modules and optionally having programmable control of transport of the selected addressable chemical wells. The addressable wells are commonly organized or integrated into a plurality of addressable plates.

One of the disadvantages of many conventional reagent transporting and storage systems used in conjunction with automated chemical analyzers is that they do not provide a refrigerated environment for receiving and storing multiple reagent packs in such a manner that each stored pack can be randomly accessed and brought from the storage position to the pipetting position. Another disadvantage of many conventional reagent transporting and storage systems is that they have only limited capacities in that they often can service only one single pipetter. They are unable to leave a reagent pack in a pipetting position while moving another reagent pack to another pipetter.

Therefore, it is desirable to provide a new method and system for transporting and sorting multiple reagent packs which can be used in conjunction with immunodiagnostic instruments and also overcome the disadvantages of conventional systems for handling reagent packs.

SUMMARY OF THE INVENTION

The present invention is directed to a new method and system for transporting and sorting multiple reagent packs used in conjunction with an immunodiagnostic instrument, and is also directed to new reagent packs used in conjunction with the new system.

It is one of the primary objects of the present invention to provide a new method and system for transporting and sorting multiple reagent packs used in conjunction with an immunodiagnostic instrument, with the capacity of providing a refrigerated environment for receiving and storing multiple reagent packs in such a manner that each stored pack can be randomly accessed and brought from the storage position to the pipetting position.

It is also a primary object of the present invention to provide a new method and system for transporting and storing multiple reagent packs used in conjunction with an immunodiagnostic instrument, with the capacity of servicing multiple pipetting stations by leaving one reagent pack in one pipetting station while moving another reagent pack to another pipetting station.

It is another one of the primary objects of the present invention to provide a new reagent pack to be used in conjunction with the new transporting and sorting system.

Accordingly, one aspect of the present invention provides a transporting and storing system to be used in conjunction with an immunodiagnostic instrument. The transporting and storing system of the present invention includes a multiplicity of reagent packs; a gantry movably mounted on a rack structure for carrying a gripper mechanism, wherein the gripper mechanism has gripping jaws for engagement with the reagent pack; a power assembly for actuating the respective movement of the gantry, the gripper mechanism and the gripping jaws; a storage nest having a multiplicity of compartments, each adapted for storing a one of the respective reagent packs; and a pipetting nest having a multiplicity of compartment, each adapted for retaining a respective one of the reagent packs for simultaneous pipetting.

The transporting and storing system of the present invention also includes at least one transport route for allowing movement of the gripper mechanism carried by the gantry for transporting the reagent packs between the storage nest and the pipetting nest.

The transporting and storing system of the present invention further includes the means for positioning and positively retaining the reagent pack by the gripper mechanism, including complementary features on the reagent pack and the gripping jaws, for causing the reagent pack to be slightly lifted up or dropped down when engaged or disengaged by the gripping jaws and moved out or in of the storage compartment.

In addition, the transporting and storing system of the present invention includes the means for maintaining precise pipetting position of the reagent pack, including spring-loaded members located in the pipetting compartment, for limiting the movement of the reagent pack during pipetting.

Another aspect of the present invention provides a transporting and storing method. The method of the present invention includes the steps of: providing a gripper mechanism having a pair of generally oppositely disposed and synchronically movable gripping jaws, each having an inner side for engagement with one of the reagent packs; mounting a gantry on a rack structure to move horizontally for carrying the gripper mechanism, such that it is vertically movable on the gantry and horizontally moveable with the gantry; aligning a multiplicity of storage compartments in vertical columns and horizontal rows for storing the reagent packs respectively; and aligning a multiplicity of pipetting compartment in at least one horizontal row for simultaneous pipetting, while leaving at least one vertical transport route between two adjacent and spaced apart columns of the compartments for allowing the vertical movement of the gripper mechanism, and at least one horizontal transport route between two adjacent and spaced apart rows of the compartments for allowing the horizontal movement of the gripper mechanism carried by the gantry, for transporting the reagent packs between the storage compartments and the pipetting compartments.

The transporting and storing method of the present invention also includes the steps of moving the gripper mechanism along the at least one vertical route and the at least one horizontal route to transport the reagent packs between the storage compartments and the pipetting compartments, and while leaving one of the reagent packs in a respective one of the pipetting compartment for pipetting, moving the gripper mechanism to transport another one of the reagent packs to another one of the pipetting compartments for simultaneous pipetting.

The transporting and storing method of the present invention further includes the steps of positioning and positively retaining the reagent pack with the gripper mechanism by utilizing holes with a tapered conical opening on the reagent pack and complementary conical pins on the gripping jaws, such that the reagent packs are slightly lifted up when being moved in and out of their respective the storage compartments to avoid direct contact therebetween, and maintaining precise pipetting position of the reagent pack by utilizing spring-loaded v-shaped members located in the pipetting compartments for limiting the movement of the reagent pack during pipetting.

A further aspect of the present invention provides a reagent pack used in conjunction with a transporting and storing system for an immunodiagnostic instrument, where the transporting and storing system has a gripper mechanism with inwardly protruding pins for positioning and positively retaining the reagent pack. The reagent pack of the present invention has an elongated body having sufficient thickness for having at least one well, where the elongated body has a slim profile with a wide middle portion, a narrow front portion with a pointed front end, and a narrow ear portion with a rounded rear end having two generally opposite outer sides.

The reagent pack of the present invention also has the means for facilitating the position and the positive retention of the reagent pack by the gripper mechanism, including complementary holes on the outer sides of the elongated body for engagement with the inwardly protruding pins of the gripping mechanism of the transporting and storing system.

As explained in greater detail below, the new system of the present invention is well suited for receiving and storing multiple reagent packs in a refrigerated environment in such a manner that each stored reagent pack can be randomly accessed and brought from the storage to a pipetting position. This is accomplished in such a manner that requires minimal footwork and a degree of freedom.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
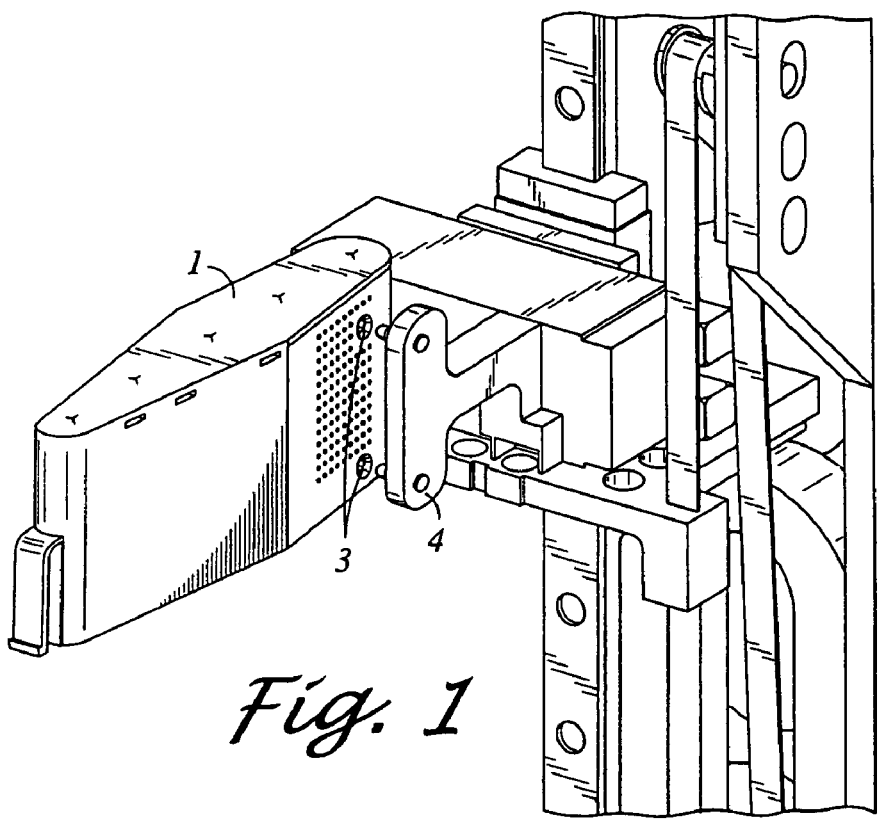
FIG. 1 is a perspective view of a reagent pack and the gripper mechanism of the transporting and storing system of the present invention, showing the alignment pins of the gripper mechanism disengaged from the reagent pack.
Figure 2:
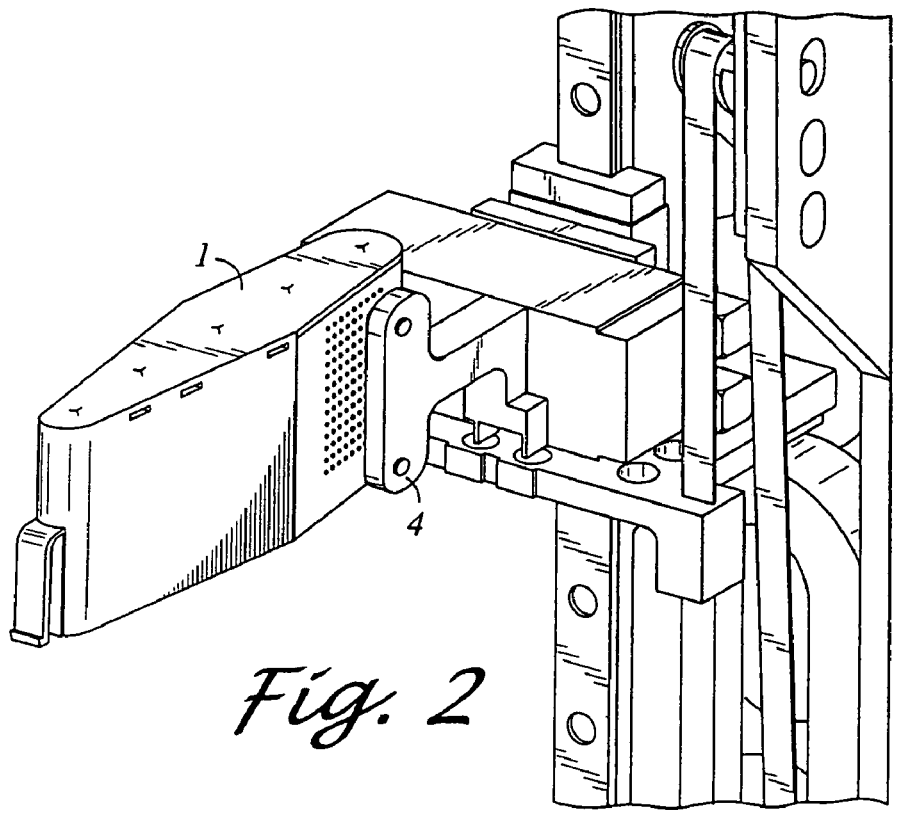
FIG. 2 is a perspective view of a reagent pack and the gripper mechanism of the transporting and storing system of the present invention, showing the alignment pins of the gripper mechanism engaged with the reagent pack.
Figure 3:
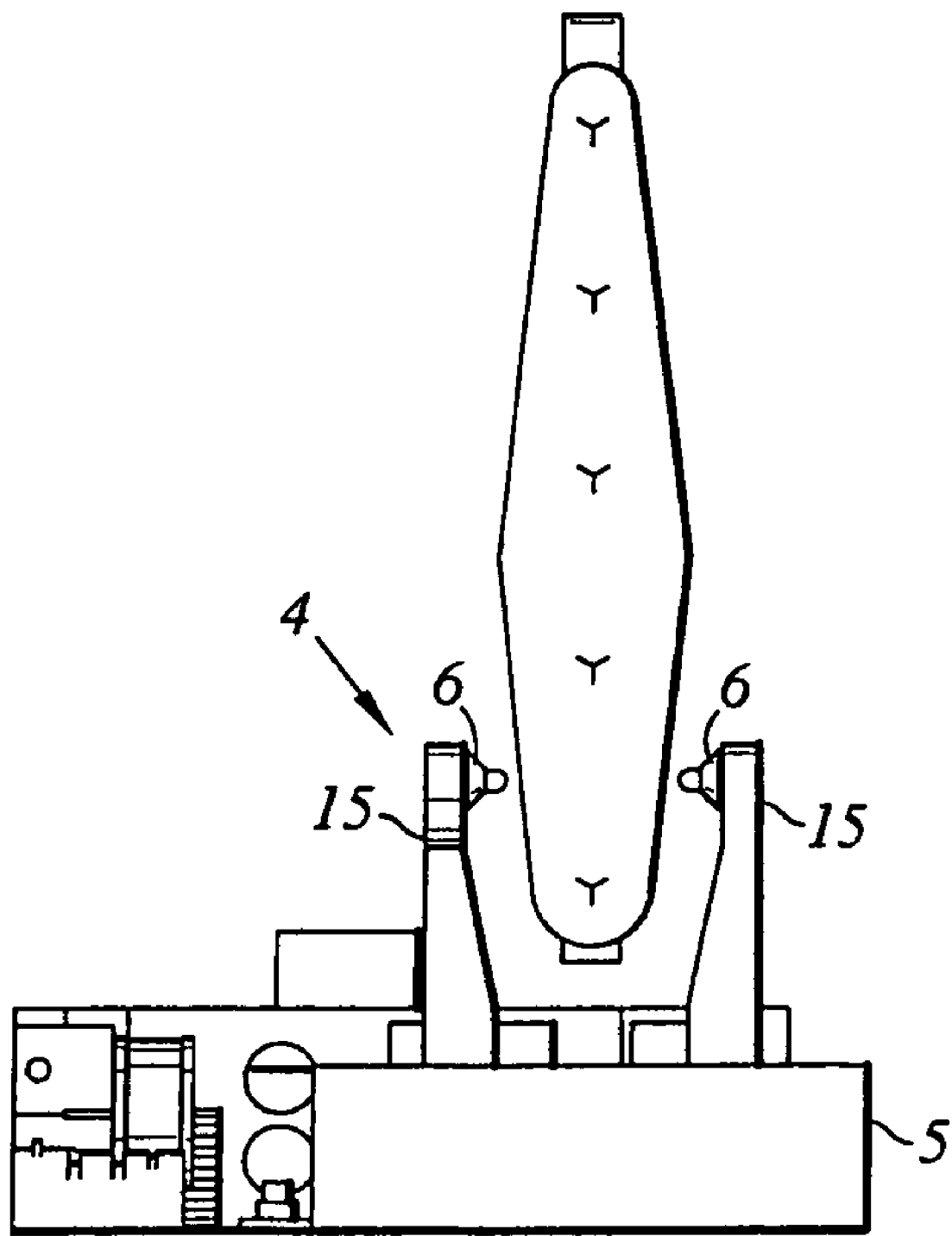
FIG. 3 is a top view of the gripper mechanism of the transporting and storing system of the present invention, showing the conical shaped alignment pins.

The present invention provides a new method and system for transporting and sorting multiple reagent packs used in conjunction with an immunodiagnostic instrument.

Referring to FIGS. 1 through 4, the transporting and storing system of the present invention includes a reagent pack 1. The reagent pack 1 has an elongated body having a sufficient thickness and a slim profile with a wide middle portion, a narrow front portion with a pointed front end, and a narrow rear portion with a rounded rear end. One or more wells are provided on the elongated body for containing reagents, samples and/or other fluids.

On the outer sides of the rear portion, a gripper mechanism 4 is provided as part of a means for positioning of and positively retaining the reagent pack. In a preferred embodiment, the facilitating means includes three conically tapered holes 2 and 3. One conically tapered hole 2 is located at one outer side of the rear portion and the other two conically tapered holes 3 are located at the other (substantially opposite) outer side of the rear portion of the reagent pack 1. In a preferred embodiment, the conically tapered holes are circular, or they can form elongated slots, or a combination of both.

The gripper mechanism 4 of the transporting and storing system of the present invention may be pneumatic or another kind, and is vertically movably supported on a gantry 5, which in turn is horizontally movably supported by a rack structure. The gripper mechanism 4 includes a pair of opposite gripping jaws 15 with synchronized motion. Of course, the motion may be accomplished by utilizing other types of arrangement and power sources which are not limited to pneumatic power.

The complementary part of the means for positioning of and positively retaining the reagent pack 1 is provided on the inner sides of the gripping jaws 15. In the preferred embodiment, the complementary part includes three conically shaped pins 6. One conically shaped pin 6 is located at the inner side of one of the gripper jaws 15 for engagement with the conically tapered hole 2 of the reagent pack 1, and the other two conically shaped pins 6 are located at the inner side of the opposite gripper jaw 15 for engagement with the conically tapered holes 3 of the reagent pack 1.

Of course, the holes 2 and 3 and the pins 6 of the complementary means for positioning and positively retaining the reagent packs by the gripper mechanism may be of other shapes, such as spherical, prismical, etc. What is important is that the entrance of the holes 2 and 3 on the reagent pack 1 are tapered (e.g., with a beveled larger opening), thereby increasing the tolerance of the gripper mechanism 4 with regard to the position of the reagent pack 1, and allowing for engagement between the pins 6 and the holes 2 and 3, respectively, even when the reagent pack 1 is not precisely positioned. A slightly misaligned reagent pack 1 can still be engaged by the pins 6 because the tapered recess of the holes 2 and 3 provides an increased engagement area for the pins 6. Once the pins 6 begin engagement with the tapered recess of the holes 2 and 3, the compression of the gripping jaws 15 will force the pins 6 to further extend into the holes 2 and 3, respectively, thereby causing the reagent pack 1 to be aligned with the gripper mechanism 4. Of course, the amount of misalignment tolerable by the gripper mechanism depends on the amount of taper in the conically tapered holes 2 and 3.

In addition, in a preferred embodiment, each pin 6 has a straight cylindrical section at its end. This feature ensures positive retention of the reagent pack by the gripper mechanism 4 in the event that there is a loss in the power to the system, which may result in a loss of compression force of the gripping jaws 15 needed for engagement of the jaws 15 with the reagent pack 1. With the cylindrical section of the pins 6 being extended into the holes 2 and 3, the reagent pack 1 will be hanging on the pins 6 of the gripper mechanism, 4 even when it is not compressed by the gripping jaws 15.

Furthermore, when the gripper mechanism 4 is engaged with the reagent pack 1, the three pins 6 define a plane which precisely orients the reagent pack 1 during transportation by the gantry 5 from one position to another.

In an alternative embodiment, the gripper mechanism 4 contains conically tapered holes which engage pins located on the reagent pack 1. In other respects, the operation of the gripper mechanism and reagent pack for this embodiment is the same.

The transporting and storing system of the present invention also includes a multi-unit storage nest 7 having a plurality of vertically and horizontally spaced compartments 8, each adapted to receive and hold a reagent pack 1. Additionally, the system includes a pipetting nest 9 also having multiple compartments 10 for positioning a reagent pack 1 for pipetting. Both nests 7 and 9 are designed to hold the reagent pack within the tolerance limits but without rigidly defining its position, as will be described in detail below.

Figure 4:
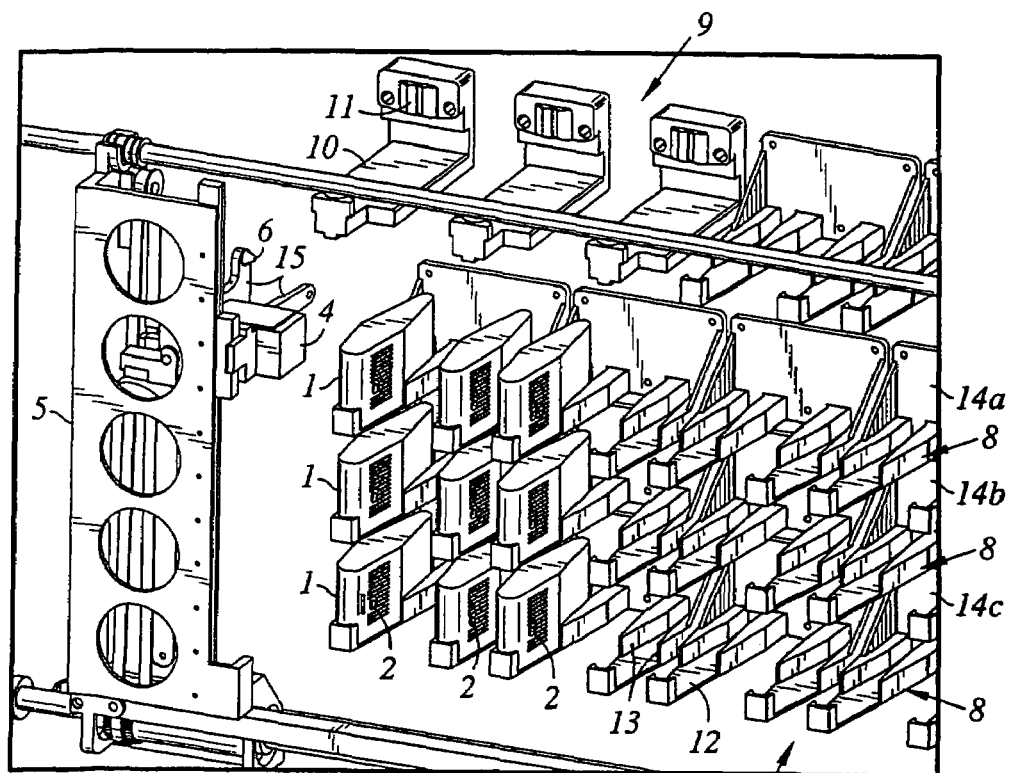
FIG. 4 is a perspective view of the gripper mechanism, the storage nest and the pipetting nest of the transporting and storing system of the present invention, showing the gripper mechanism at its initial position.

Referring to FIG. 4, the storage nest 7 has a multiplicity of compartments 8 arranged in multiple vertical columns, where the respective compartments in the multiple columns are also aligned in horizontal rows, thereby forming a two-dimensional matrix, such that when the reagent packs 1 are held in the storage nest 7, they are aligned in vertical columns and horizontal rows. One or more empty or open vertical "transport routes" (with no compartment) are provided to allow the gripper mechanism 4 to transport the reagent packs 1 vertically within the storage nest 7 and between the storage nest 7 and the pipetting nest 9. Similarly, one or more empty or open horizontal "transport routes" are also provided to allow the gripper mechanism 4 to transport the reagent packs 1 horizontally.

Each compartment 8 of the storage nest 7 has a flat bottom 12 and two substantially opposite and vertical sidewalls 13. The clearance between the retaining sidewalls 13 of the compartment 8 and the reagent pack 1 held therein provides limits to the horizontal motion of the reagent pack 1.

When a reagent pack 1 is sent into a compartment 8 by the gripper mechanism 4, a small gap is intentionally maintained between the flat bottom 12 of the compartment 8 and the bottom of the reagent pack 1, as long as the pins 6 of the gripper mechanism 4 are still engaged with the holes 2 and 3 of the reagent pack 1. With this arrangement, any direct contact between the flat bottom 12 of the compartment 8 and the bottom of the reagent pack 1 is avoided, as the reagent pack 1 is sent into the compartment 8 of the storage nest 7, thereby eliminating interference therebetween that is a result of mechanical part tolerances.

Once the reagent pack 1 is positioned within the compartment 8 between the two sidewalls 13 and above the flat bottom 12, the pins 6 of the gripper mechanism 1 are synchronously disengaged from the holes 2 and 3 of the reagent pack 1, which allows the reagent pack 1 to drop down the distance of the small gap and rest on the flat bottom 12 of the compartment 8.

When the reagent pack 1 needs to be removed from the compartment 8, the gripping jaws 15 of the gripper mechanism 4 are moved in to be adjacent to the rear end of the reagent pack 1 and are ready to retrieve the reagent pack 1. However, the pins 6 of the gripper mechanism 4 are intentionally positioned slightly higher than the center of the holes 2 and 3 of the reagent pack 1 but still within the range of tapered openings of the holes 2 and 3, such that when the gripping jaws 15 are compressed, the pins 6 are engaged with and guided by the tapered surfaces to finally align with and insert into the holes 2 and 3 and, during this process of engagement, causes the reagent pack 1 to be lifted up slightly, such that the same small gap is left between the bottom of the reagent pack 1 and the flat bottom 12 of the compartment 8. This arrangement prevents any direct contact between the flat bottom 12 of the compartment 8 and the bottom of the reagent pack 1 and thereby eliminates any interference therebetween as the reagent pack 1 is retrieved from the compartment 8 of the storage nest 7.

The pipetting nest 9 has a multiplicity of compartments 10 aligned in a horizontal row. Each compartment 10 has a spring-loaded v-block 11 for engaging the pointed front end of the reagent pack 1 for its precise positioning. This is because, during pipetting, the reagent pack 1 has to be positioned with a relatively high precision and it has to be retained both horizontally and vertically.

When the pins 6 of the gripper mechanism 4 are engaging the reagent pack 1, the v-block 11 translates to a position defined by the retained reagent pack 1. When the pins 6 are disengaged from the reagent pack 1, the v-block 11 springs back against rigid stops, which are placed at a distance that is slightly greater than the length of the pack 1. As a result, the reagent pack 1 moves into a position within the limits defined by the v-block 11. The v-block 11 limits the motion of the reagent pack 1 when a pipetter tip is withdrawn from the pack as the elastomeric seal of the reagent pack 1 creates a drag, which tends to cause the reagent pack 1 to be lifted up. After the pipetter tip is withdrawn, the reagent pack 1 is free to fall back down into its position in the compartment 10 of the pipetting nest 9, which prevents the pipetter tip from contacting the bottom of the wells of the reagent pack 1 during future assays.

Figure 5:
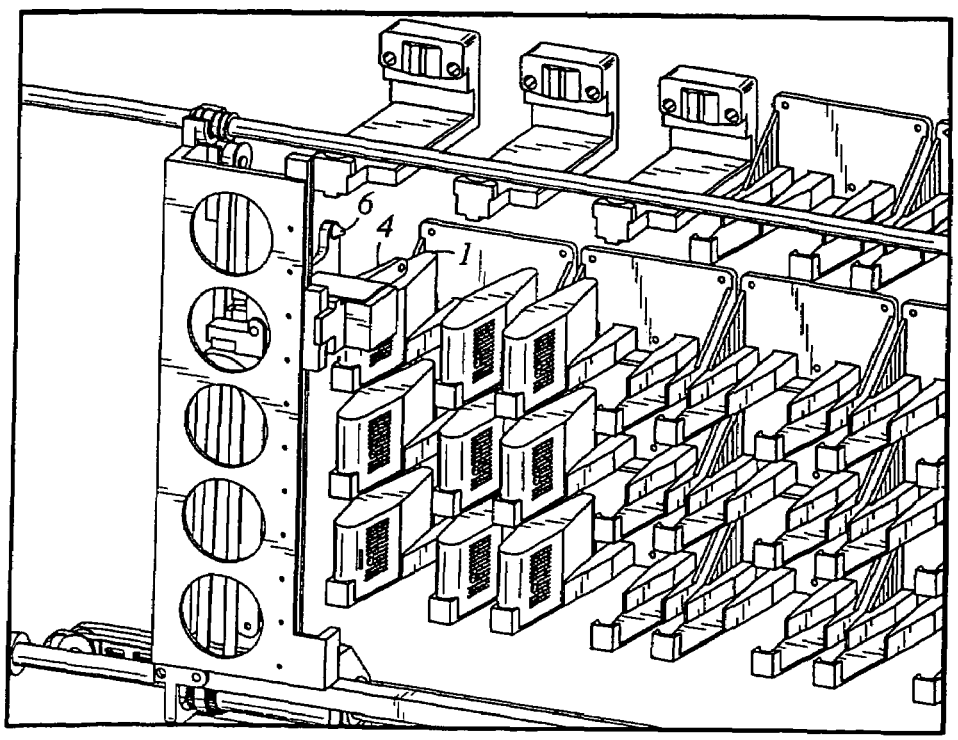
FIG. 5 is a perspective view of the gripper mechanism, the storage nest and the pipetting nest of the transporting and storing system of the present invention, showing the first step of the transporting and storing method of the present invention where the gripper mechanism moves in a horizontal transport route of the storage nest to a desired column of reagent packs held in the storage nest.

Referring to FIGS. 4 through 15, the transporting and storing method of the present invention includes the following steps:

1. Starting from its initial position, as shown in FIG. 4, the gantry 5 with the gripper mechanism 4 moves horizontally through a horizontal transport route 14a, positions itself over the desired column of reagent packs 1, and opens its gripping jaws 15, as shown in FIG. 5.

Figure 6:
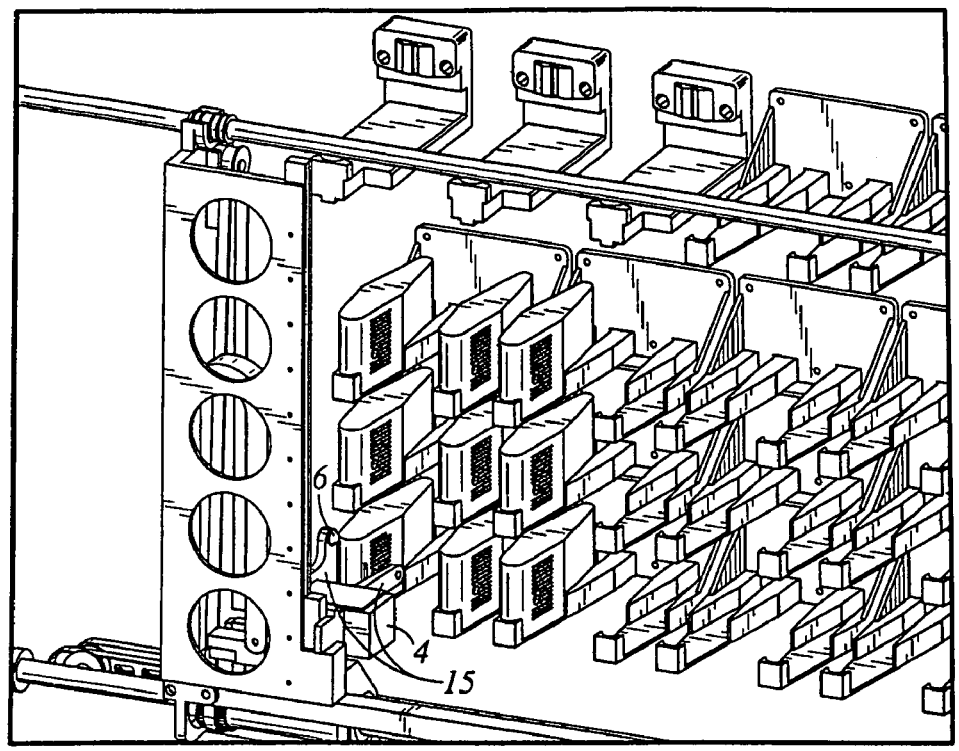
FIG. 6 is a perspective view of the gripper mechanism, the storage nest and the pipetting nest of the transporting and storing system of the present invention, showing the second step of the transporting and storing method of the present invention where the gripper mechanism moves in a vertical transport route of the storage nest to a desired reagent pack held in a compartment of the storage nest.

2. The gripper mechanism 4 moves down vertically until it reaches the desired reagent pack 1. It stops when the pins 6 of the gripping jaws 15 are positioned at approximately 0.03 inch above the center of the holes 2 and 3 of the reagent pack 1, as shown in FIG. 6.

Figure 7:
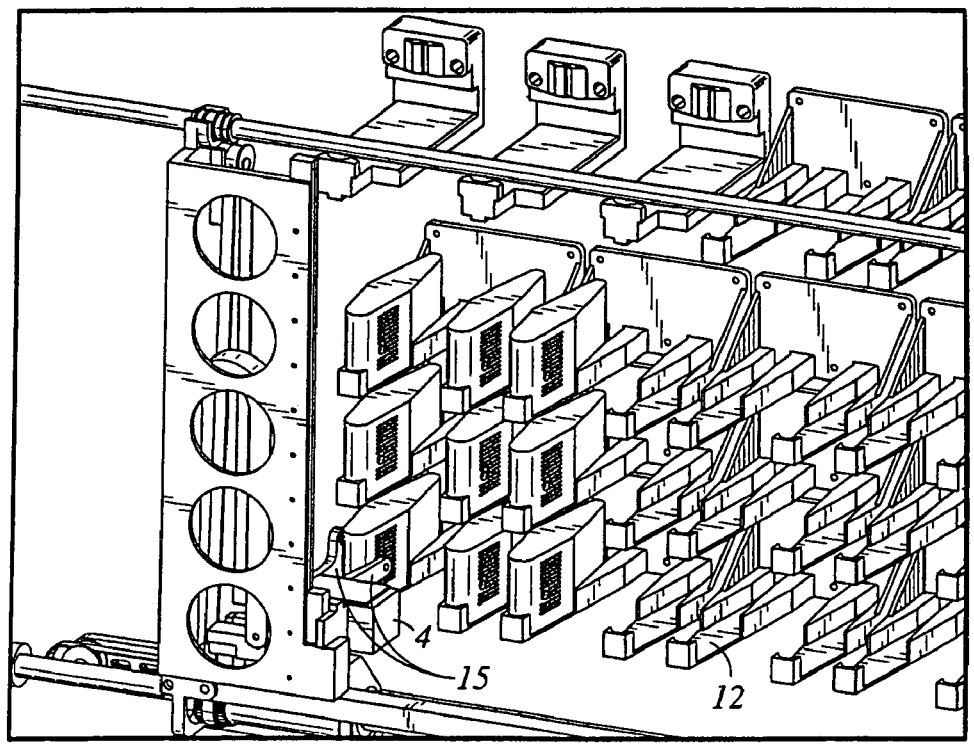
FIG. 7 is a perspective view of the gripper mechanism, the storage nest and the pipetting nest of the transporting and storing system of the present invention, showing the third step of the transporting and storing method of the present invention where the gripper mechanism engages and lifts up the desired reagent pack from the bottom of the compartment of the storage nest.

3. The gripper mechanism 4 is actuated and the gripping jaws 15 move synchronously towards each other until the pins 6 are fully engaged with the holes 2 and 3 of the reagent pack 1. As a result, the reagent pack 1 is raised an amount necessary to compensate for position error caused by tolerance accumulation at a position defined by the pins 6 above the flat bottom 12 of the compartment 8 of the storage nest 7, as shown in FIG. 7.

Figure 8:
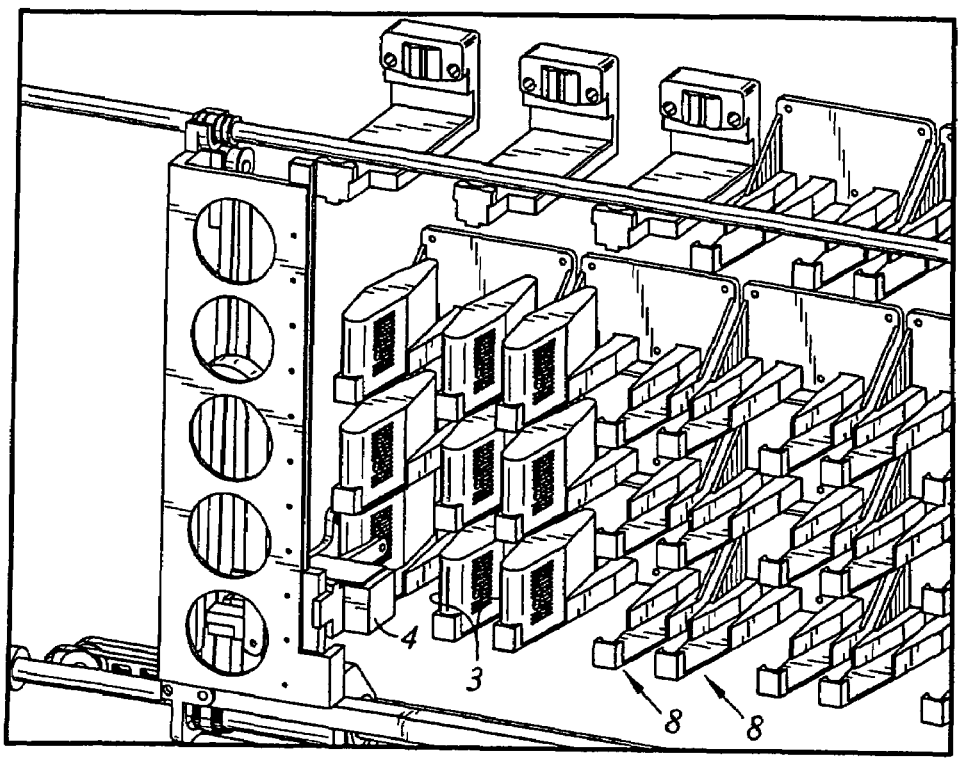
FIG. 8 is a perspective view of the gripper mechanism, the storage nest and the pipetting nest of the transporting and storing system of the present invention, showing the fourth step of the transporting and storing method of the present invention where the gripper mechanism moves the reagent pack out of the compartment of the storage nest.

4. The gripper mechanism 4 moves vertically until the bottom of the reagent pack 1 is just above the sidewalls 13 of the compartment 8 of the storage nest 7, as shown in FIG. 8.

Figure 9:
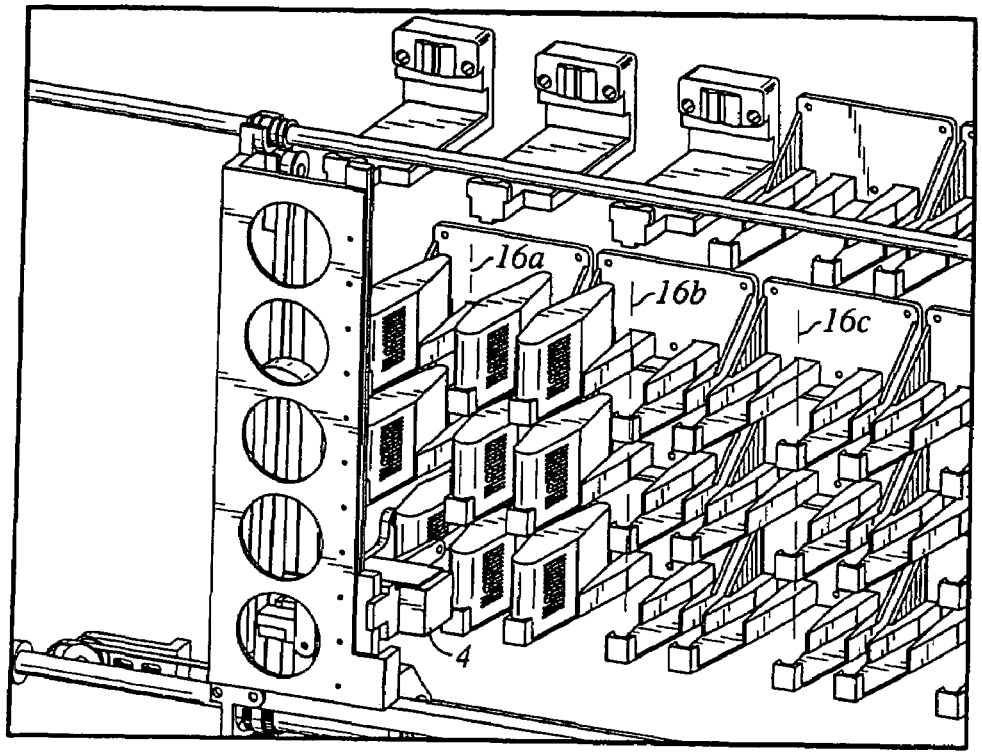
FIG. 9 is a perspective view of the gripper mechanism, the storage nest and the pipetting nest of the transporting and storing system of the present invention, showing the fifth step of the transporting and storing method of the present invention where the gripper mechanism moves the reagent pack to a nearby vertical transport route of the storage nest.

5. The gripper mechanism 4 then moves the reagent pack 1 horizontally to a nearest vertical transport route 16a, as shown in FIG. 9.

Figure 10:
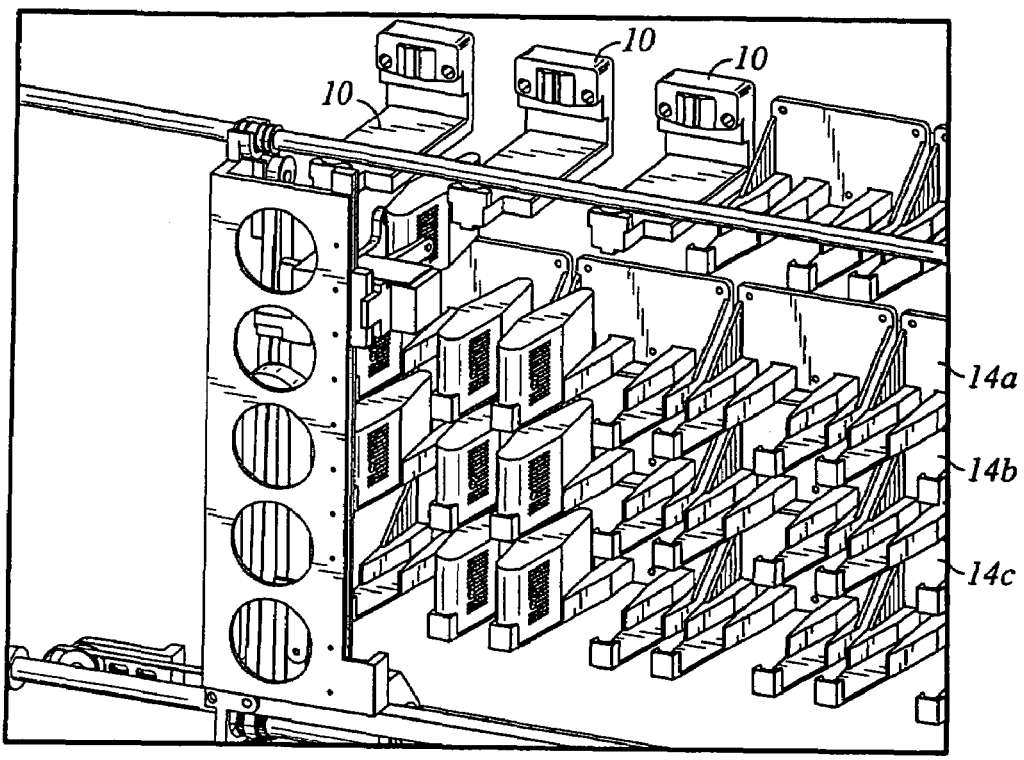
FIG. 10 is a perspective view of the gripper mechanism, the storage nest and the pipetting nest of the transporting and storing system of the present invention, showing the sixth step of the transporting and storing method of the present invention where the gripper mechanism moves the reagent pack in the vertical transport route of the storage nest up to the horizontal transport route.

6. The gripper mechanism 4 moves the reagent pack 1 vertically up in the vertical transport route to the horizontal transport route 14a, as shown in FIG. 10.

Figure 11:
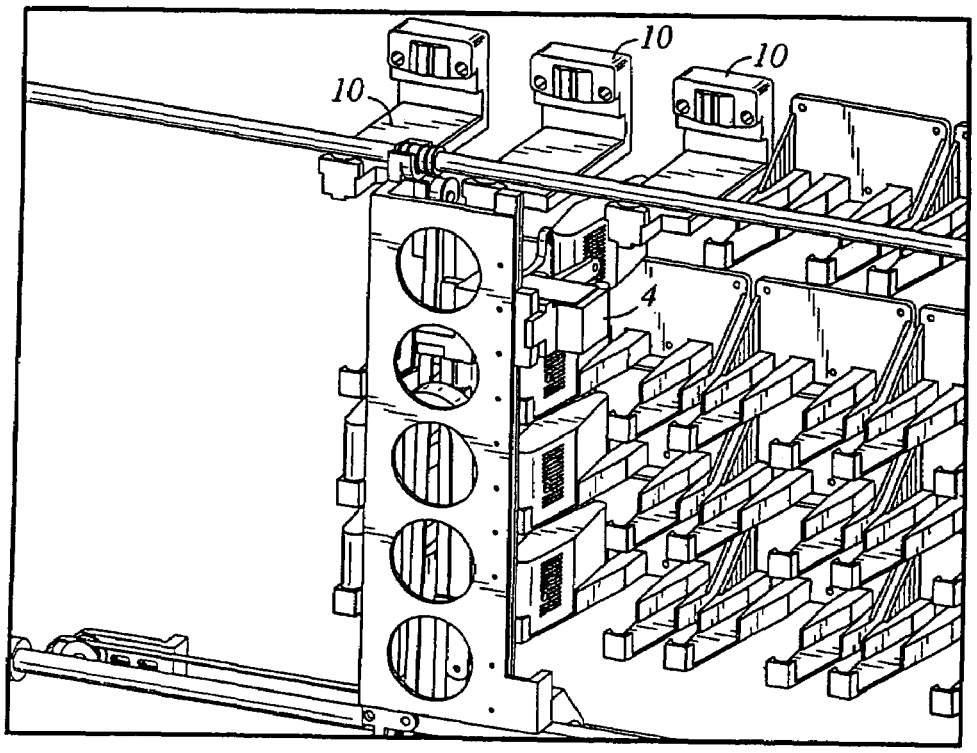
FIG. 11 is a perspective view of the gripper mechanism, the storage nest and the pipetting nest of the transporting and storing system of the present invention, showing the seventh step of the transporting and storing method of the present invention where the gripper mechanism moves the reagent pack in the horizontal transport route of the storage nest to a vertical transport route next to an available compartment of the pipetting nest.

7. The gripper mechanism 4 moves the reagent pack 1 horizontally in the horizontal row to a vertical transport route next to one of the available compartments 10 of the pipetting nest 9, as shown in FIG. 11.

Figure 12:
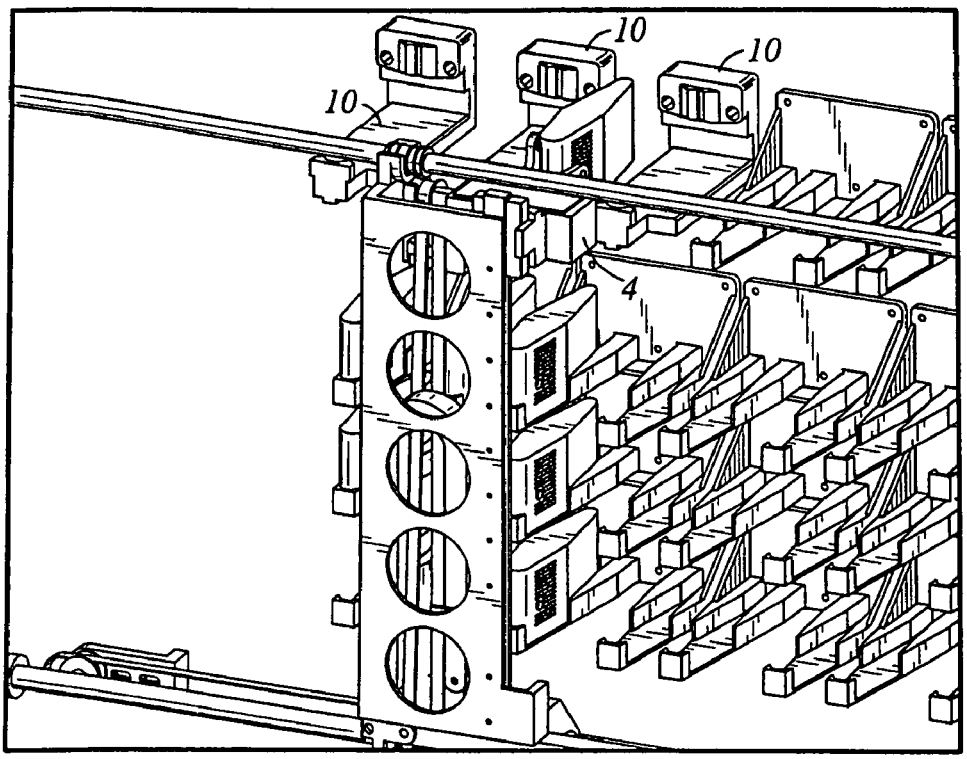
FIG. 12 is a perspective view of the gripper mechanism, the storage nest and the pipetting nest of the transporting and storing system of the present invention, showing the eighth step of the transporting and storing method of the present invention where the gripper mechanism moves the reagent pack in the vertical transport route next to the available compartment of the pipetting nest to a position close to the available compartment of the pipetting nest.

8. The gripper mechanism 4 moves vertically in the transport route next to the available compartment 10 of the pipetting nest 9 until the bottom of the reagent pack 1 is above the bottom of the compartment 10, as shown in FIG. 12.

Figure 13:
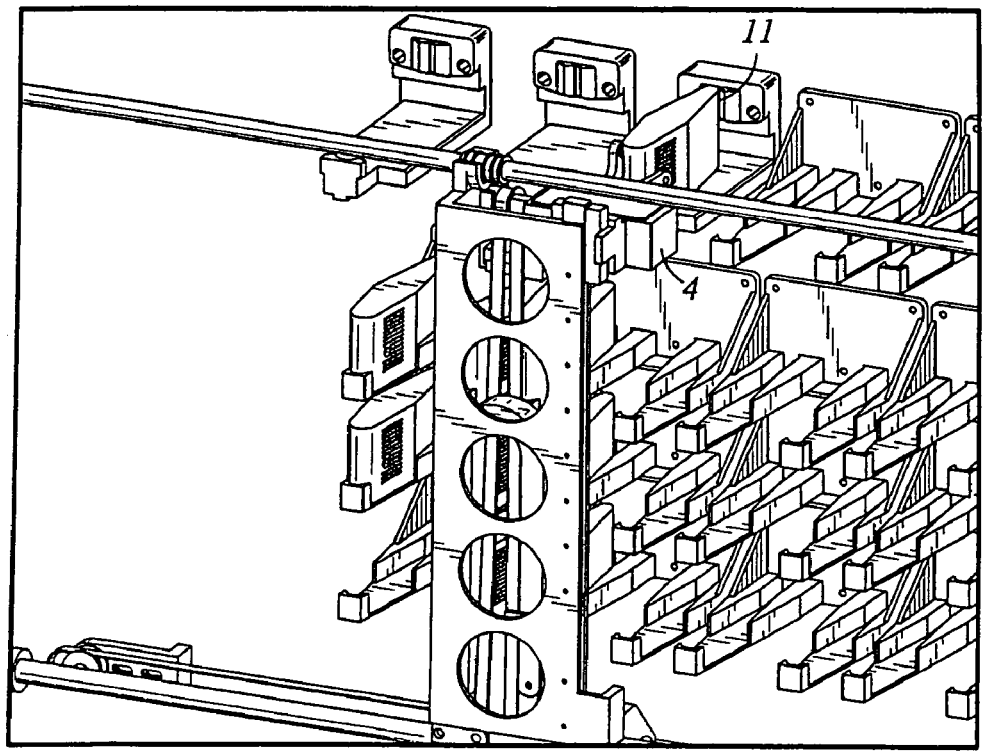
FIG. 13 is a perspective view of the gripper mechanism, the storage nest and the pipetting nest of the transporting and storing system of the present invention, showing the ninth step of the transporting and storing method of the present invention where the gripper mechanism moves the reagent pack horizontally into the compartment of the pipetting nest to engage with the spring-loaded v-blocks thereof.

9. The gripper mechanism 4 moves the reagent pack 1 horizontally into the compartment 10 of the pipetting nest 9 and deflects the spring-loaded v-blocks 11 until the reagent pack 1 is centered in the compartment 10 of the pipetting nest 9, as shown in FIG. 13.

Figure 14:
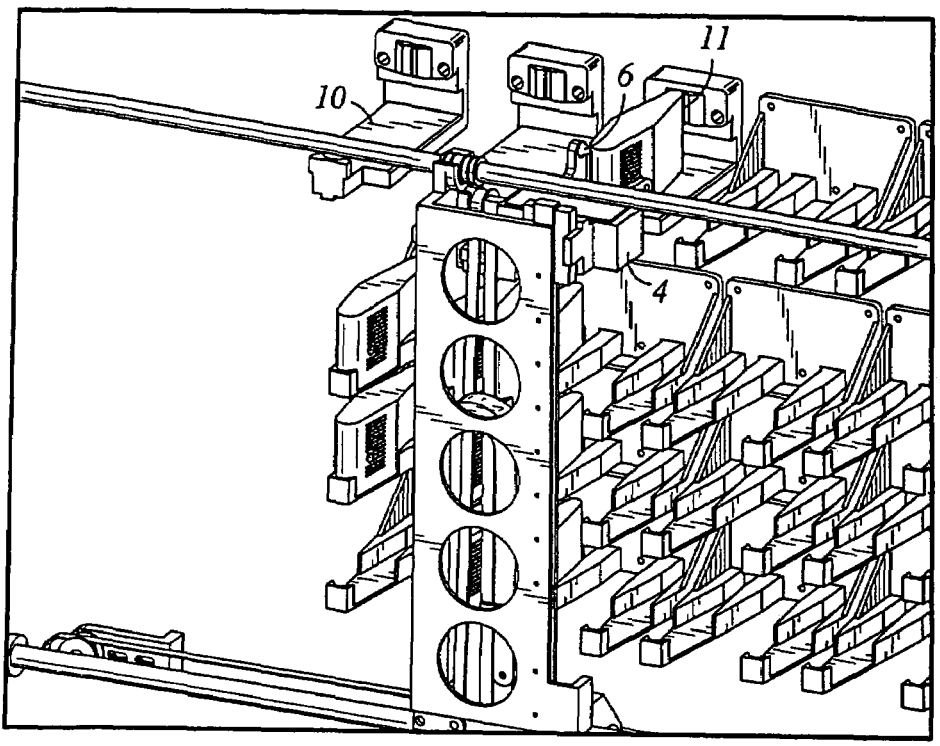
FIG. 14 is a perspective view of the gripper mechanism, the storage nest and the pipetting nest of the transporting and storing system of the present invention, showing the tenth step of the transporting and storing method of the present invention where the gripper mechanism is disengaged from the reagent pack which is retained by the spring-loaded v-blocks and settled onto the bottom of the compartment of the pipetting nest.

10. The gripper mechanism 4 reverses and its pins 6 disengage from the reagent pack 1. The v-blocks 11 return to their hard stops and align the reagent pack 1 to its precise pipetting position. The reagent pack 1 lowers down a small distance under gravity to come to rest on the bottom of the compartment 10 of the pipetting nest, as shown in FIG. 14.

Figure 15:
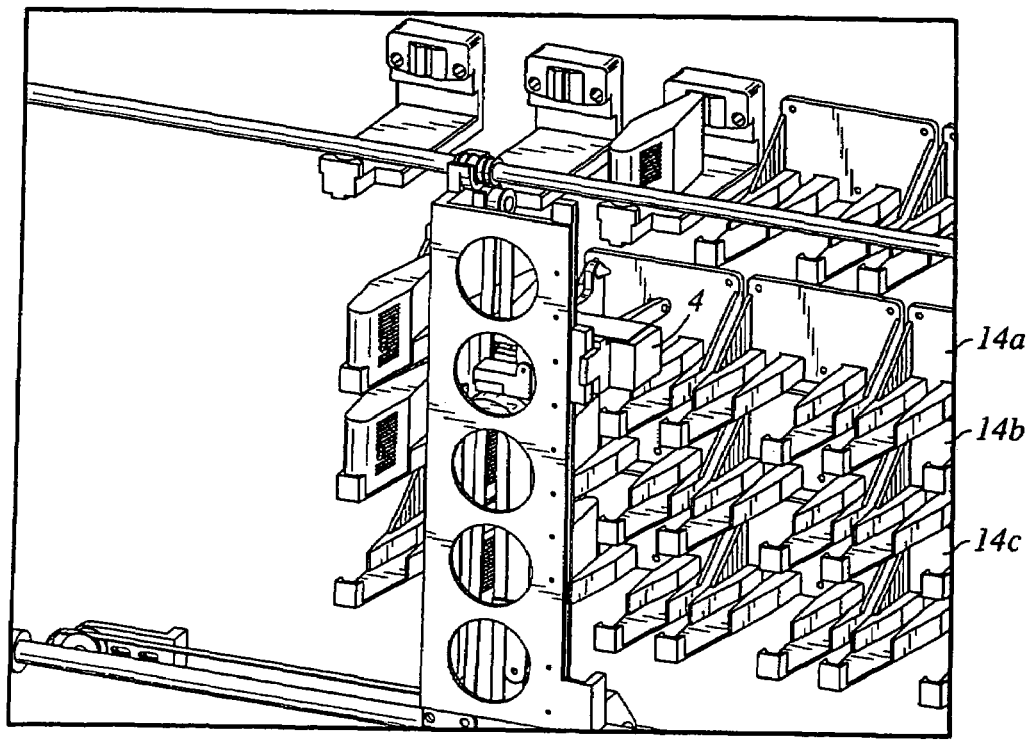
FIG. 15 is a perspective view of the gripper mechanism, the storage nest and the pipetting nest of the transporting and storing system of the present invention, showing the eleventh step of the transporting and storing method of the present invention where the disengaged gripper mechanism moves vertically to a horizontal transport route for returning to its initial position.

11. The gripper mechanism 4 moves vertically down to the horizontal transport route 14a to return to its initial position, as shown in FIG. 15.

12. While one reagent pack 1 is retained in one of the compartments 10 of the pipetting nest 9 for the pipetting procedure, the gripper mechanism 4 may repeat the above steps to transport another one of the reagent packs 1 from the storage nest 7 to another available compartment 10 of the pipetting nest 9 for simultaneous pipetting.

One of the novel features of the transporting and storing system and method of the present invention is the ability to transport a single desired pack from a storage to a pipetting position and to service multiple pipetting positions with a single transport system.

Another novel feature of the transporting and storing system and method of the present invention is the combination of the conically tapered holes on the reagent pack and the complementary matching pins on the gripper mechanism for positioning and positively retaining the reagent pack while transporting it from the storage position to the pipetting position.

It is to be understood that the form of the system depicted in FIGS. 1 through 15 has been chosen only for the purpose of describing a particular embodiment and function of the invention, and that the arrangement of the invention can be addressed in various ways and incorporated in other types of devices, all of which will be evident to those skilled in the art. It is also to be understood that the particular arrangement of the transporting and storing system of the present invention may vary depending on the immunodiagnostic instrument it is incorporated or working together with, but that the determination of necessary variation is well within the skill in the art in view of the instant disclosure.

Suitable components that are commercially available would be known to those of ordinary skill in the art in view of this disclosure.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. A transporting and storing system used in conjunction with an immunodiagnostic instrument, comprising:
   a. a multiplicity of reagent packs, each pack having a body with two generally opposite outer sides, wherein each outer side has at least one inwardly facing feature;
   b. a gantry movably mounted on a rack structure for carrying a gripper mechanism, the gripper mechanism having a pair of oppositely disposed gripping jaws moving synchronically toward or away from each other, each gripping jaw having an inner side with at least one outwardly facing feature, which extends toward the opposite gripping jaw, wherein each of said outwardly facing feature is complementary to said at least one inwardly facing feature and wherein a movement of gripping jaws toward each other causes the outwardly facing features to engage the inwardly facing features;
   c. a power assembly for actuating the respective movement of said gantry, said gripper mechanism and said gripping jaws;
   d. a storage nest having a multiplicity of compartments aligned in vertical columns and horizontal rows, each compartment adapted for storing a respective one of said reagent packs;
   e. a pipetting nest having a multiplicity of compartments aligned in at least one horizontal row, each compartment adapted for retaining a respective one of said reagent packs for simultaneous pipetting; and f. at least one transport route for allowing movement of said gripper mechanism carried by said gantry for transporting said reagent packs between said storage nest and said pipetting nest.

2. The system as defined in claim 1, wherein said power assembly comprises a pneumatic power source.

3. The system as defined in claim 1, wherein said at least one transport route comprises a vertical transport route located between two adjacent and spaced apart columns of said compartments of said storage nest.

4. The system as defined in claim 3, wherein said at least one transport route further comprises a horizontal transport route located between said at least one row of said compartments of said pipetting nest and an adjacent and spaced apart row of said compartments of said storage nest.

5. The transporting and storing system as defined in claim 1, wherein said complementary outwardly facing features are pins and inwardly facing features are complementary tapered conical holes.

6. The transporting and storing system as defined in claim 5, wherein the pins are conical, spherical, or prismical.

7. The transporting and storing system of claim 1, wherein said outwardly facing feature comprises pins and said inwardly facing feature of said reagent pack comprises complementary holes.

8. The transporting and storing system of claim 1, wherein said reagent pack comprises:

a. an elongated body having sufficient thickness for having at least one well;

b. said elongated body having a slim profile with a wide middle portion, a narrow front portion with a pointed front end, and a narrow ear portion with a rounded rear end having two generally opposite outer sides;

c. complementary holes on said outer sides of said elongated body for engagement with said inwardly protruding pins of said gripping mechanism of said transporting and storing system.

9. The transporting and storing system of claim 8, wherein said complementary holes of said reagent pack each has a tapered conical opening for causing said reagent pack to be slightly lifted up when engaged by said gripping mechanism.

* * * * *